United States Patent
Dryden et al.

(10) Patent No.: US 10,401,331 B2
(45) Date of Patent: Sep. 3, 2019

(54) GAS CHROMATOGRAPHY (GC) COLUMN HEATER

(71) Applicant: Agilent Technologies, Inc., Santa Clara, CA (US)

(72) Inventors: Paul C Dryden, Lincoln University, CA (US); Sammye Elizabeth Traudt, Middletown, DE (US); George P Walsh, Wilmington, DE (US); William H Wilson, Newark, DE (US); Richard P White, Glen Mills, PA (US); Jane Ann Leous, Philadelphia, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 574 days.

(21) Appl. No.: 14/802,874

(22) Filed: Jul. 17, 2015

(65) Prior Publication Data
US 2016/0116447 A1    Apr. 28, 2016

Related U.S. Application Data

(60) Provisional application No. 62/067,407, filed on Oct. 22, 2014, provisional application No. 62/067,924, filed on Oct. 23, 2014.

(51) Int. Cl.
*G01N 30/30*    (2006.01)
*H05B 3/20*    (2006.01)
*G01N 30/02*    (2006.01)

(52) U.S. Cl.
CPC .............. *G01N 30/30* (2013.01); *H05B 3/20* (2013.01); *G01N 2030/025* (2013.01); *G01N 2030/3007* (2013.01)

(58) Field of Classification Search
CPC ........ G01N 30/30; G01N 30/46; G01N 30/54; G01N 30/60; G01N 30/00; G01N 30/02; G01N 2030/025; G01N 2030/3007; G01N 2030/3015; G01N 2030/3053; G01N 2030/3061; G01N 2030/381;
(Continued)

(56) References Cited

U.S. PATENT DOCUMENTS 3,213,596 A    10/1965    Gill
4,923,486 A    5/1990    Rubey
(Continued)

FOREIGN PATENT DOCUMENTS

CN    201034990 Y    3/2008
CN    101595385 A    12/2009
(Continued)

OTHER PUBLICATIONS

International Search Report and Written Opinion for PCT/US2015/040999 dated Oct. 16, 2015.
(Continued)

*Primary Examiner* — Shawntina Fuqua

(57) ABSTRACT

An apparatus includes a first column heating apparatus, which includes: a first substrate; a second substrate including silicon; and a first heating element disposed between the first substrate and the second substrate. The apparatus also includes a second column heating apparatus, which includes: a third substrate; a fourth substrate including silicon; and a second heating element disposed between the third substrate and the fourth substrate.

20 Claims, 6 Drawing Sheets

(58) Field of Classification Search
CPC ......... G01N 2030/386; G01N 2030/02; H05B 3/20; H05B 3/22; H05B 3/26; H05B 3/24; H05B 3/30
See application file for complete search history.

(56) References Cited

U.S. PATENT DOCUMENTS

| | | | |
|---|---|---|---|
| 5,782,964 | A | 7/1998 | Mustacich |
| 5,808,178 | A | 9/1998 | Rounbehler et al. |
| 5,808,179 | A * | 9/1998 | Sittler .................. G01N 30/88 73/23.42 |
| 5,856,616 | A | 1/1999 | Maswadeh et al. |
| 5,939,614 | A | 8/1999 | Walters et al. |
| 6,029,498 | A | 2/2000 | Walters et al. |
| 6,068,604 | A | 5/2000 | Krause et al. |
| 6,171,378 | B1 | 1/2001 | Manginell et al. |
| 6,454,840 | B1 | 9/2002 | Gellert et al. |
| 6,485,543 | B1 | 11/2002 | MacDonald et al. |
| 6,607,580 | B1 | 8/2003 | Hastings et al. |
| 6,666,907 | B1 | 12/2003 | Manginell et al. |
| 6,966,212 | B2 | 11/2005 | Klee et al. |
| 7,396,468 | B2 | 7/2008 | Boyes et al. |
| 7,513,936 | B2 | 4/2009 | Roques |
| 9,194,849 | B2 | 11/2015 | Kanai et al. |
| 2003/0228452 | A1 | 12/2003 | Yu |
| 2006/0283324 | A1 | 12/2006 | Roques |
| 2007/0266858 | A1 | 11/2007 | Alm et al. |
| 2009/0272270 | A1 | 11/2009 | McGill et al. |
| 2010/0044288 | A1 | 2/2010 | Kitagawa |
| 2010/0243635 | A1 | 9/2010 | Nakamura et al. |
| 2012/0160038 | A1 | 6/2012 | Wells et al. |
| 2013/0043380 | A1 | 2/2013 | Correale |
| 2014/0119993 | A1 | 5/2014 | Rhodes |
| 2014/0290491 | A1 | 10/2014 | Kanai et al. |
| 2015/0153314 | A1 * | 6/2015 | Karoum .................. G01N 30/46 73/23.36 |

FOREIGN PATENT DOCUMENTS

| | | |
|---|---|---|
| CN | 201532334 U | 7/2010 |
| CN | 104101670 A | 10/2014 |
| JP | 61288154 A | 12/1986 |
| JP | 05036363 U | 5/1993 |
| JP | 2004146568 A | 5/2004 |
| JP | 2004363335 A | 12/2004 |
| JP | 2013238572 A | 11/2013 |
| WO | 2008094030 A1 | 8/2008 |

OTHER PUBLICATIONS

PCT International Search Report and The Written Opinion of the International Searching Authority regarding PCT/US2015/041004 dated Oct. 19, 2015.
Wang, A., et al., "Gas Chromatography Using Resistive Heating Technology," Journal of Chromatography A, 2012, vol. 1261, pp. 46-57.
International Search Report for PCT/US2015/040995.
Extended European Search Report dated Jan. 25, 2018, Application No. 15839582.2 , 8 pages.
Han, et al.,"SOG-Si Purification Technology and Equipment," (1st Ed.), Metallurgical Industry Press, 2011, 3 pages.
Zhao, et al., "AlN-BN Study on Fabrication of AlN-BN Composites and Its Dielectric Properties and Thermal Conductivity," Chinese Master's Theses Full-text Database Engineering Science and Technology I, 2007, 6 pages.

* cited by examiner

GAS CHROMATOGRAPHY (GC) COLUMN HEATER

CROSS-REFERENCE TO RELATED APPLICATIONS

The present application claims priority under 35 U.S.C. § 119(e) from: U.S. Provisional Application No. 62/067,924 filed on Oct. 23, 2014, naming Paul Dryden, et al. as inventors; and U.S. Provisional Patent Application No. 62/050,125 filed on Sep. 13, 2014, naming Sammye Traudt, et al. as inventors. The entire disclosures of U.S. Provisional Patent Application Nos. 62/050,125 and 62/067,924 are specifically incorporated herein by reference.

BACKGROUND

In GC systems, the amount of time required for a chemical compound to traverse the entire length of a separation column ("column") is known as its retention time. One factor that contributes to the retention time of a chemical compound is the temperature of the separation column. Controlling the temperature of the column precisely from analysis to analysis is beneficial to provide repeatability in the retention time for a particular chemical compound, or analyte. In addition, programmatically changing the column temperature while the sample analytes are migrating through it can advantageously provide shorter analysis time and reduce peak broadening.

Often, columns are heated in known systems using an air convection oven because of its ability to provide a uniform and repeatable thermal environment in a space large enough to accommodate a wide variety of column diameters and lengths. The columns are typically arranged on a support structure that creates an open cylinder. This allows the heated air access over all the column surfaces and results in uniform temperatures across the entire column length. While air convection ovens are useful, their use comes with clear disadvantages. For example, convection ovens require a significant amount of energy and time to heat up, and a significant amount of time to cool down. This leads, of course, to comparatively long cycle times and high power consumption, among other disadvantages. In addition, the ability to do rapid analysis via temperature programmed conditions is limited when using air convection ovens.

What is needed, therefore, is an apparatus that overcomes at least the drawbacks of known GC column heaters discussed above.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

Figure 1:
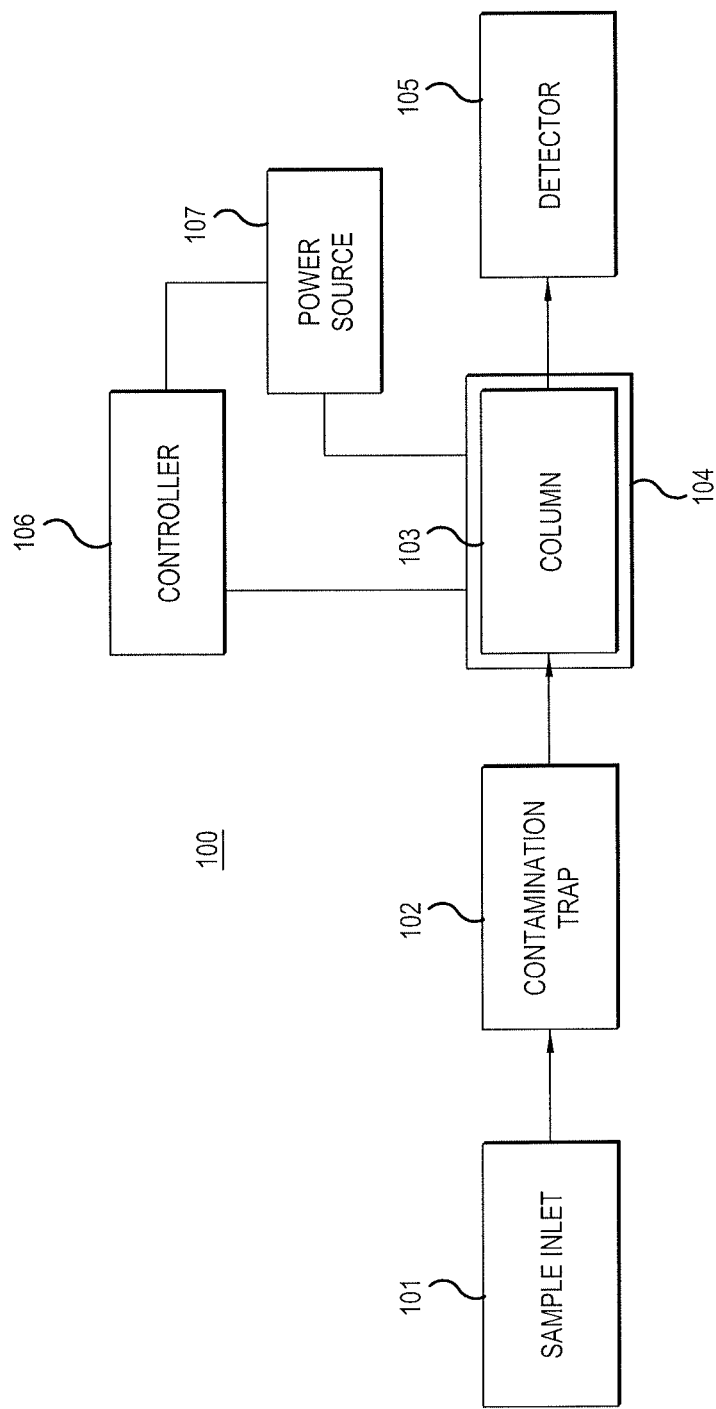
FIG. 1 is a simplified block diagram of a GC system in accordance with a representative embodiment.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms 'a', 'an' and 'the' include both singular and plural referents, unless the context clearly dictates otherwise. Thus, for example, 'a device' includes one device and plural devices.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

As used in the specification and the appended claims and in addition to its ordinary meaning, the term 'approximately' means to within an acceptable limit or amount to one having ordinary skill in the art. For example, 'approximately the same' means that one of ordinary skill in the art would consider the items being compared to be the same.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials and methods that are within the purview of one of ordinary skill in the art may be used in accordance with the representative embodiments.

Relative terms, such as "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be "below" that element. Similarly, if the device were rotated by 90° with respect to the view in the drawings, an element described "above" or "below" another element would now be "adjacent" to the other element; where "adjacent" means either abutting the other element, or having one or more layers, materials, structures, etc., between the elements. As used herein, an element "disposed over" or "disposed below" another element means the element is "adjacent to" another element. "Directly adjacent" means abutting the other element.

FIG. 1 is a simplified block diagram of a GC system 100 in accordance with a representative embodiment. Many aspects of the GC system 100 are known to one of ordinary skill in the art. As such, details of certain known components of the GC system 100 are omitted. In certain instances representative examples of known components that may be implemented are noted, but are presented for illustration and are, in no way, intended to be limiting.

The GC system 100 comprises a sample inlet 101. The sample inlet 101 is fluidically coupled to a contaminant trap 102. The contaminant trap 102 is fluidically coupled to a column 103, which may be one of a variety of columns useful in gas chromatography. In an embodiment, the contaminant trap 102 may be as described in concurrently filed, commonly owned U.S. patent application Ser. No. 14/057,022 (filed Oct. 18, 2013), the disclosure of which is specifically incorporated herein by reference. The contaminant trap 102 is a microfluidic contaminant trap configured to trap contaminants in the sample from the sample inlet 101 and to prevent the trapped contaminants from reaching the column 103. It is noted that the inclusion of contaminant trap 102 is merely illustrative, and the present teachings are contemplated for use in GC systems that do not comprise a contaminant trap, or that do not comprise a microfluidic contaminant trap as described in the application referenced immediately above.

The column 103 separates the components of a chemical sample. The column 103 may be a capillary column comprising a piece of fused silica or metal tubing (not shown) with a coating on the inner portions of the tubing or packed with particles that interact with the sample from sample inlet 101 to separate the components of the chemical sample.

The column 103 is provided in contact with a column temperature control apparatus 104, which will be described more fully below in connection with representative embodiments. By virtue of the column temperature control apparatus 104, the retention time for analytes is controlled, while the uniformity of the heating of the column 103 is comparatively improved. These and other benefits of the column temperature control apparatus 104 are described more fully below in connection with representative embodiments.

The column 103 is connected to a detector 105, which detects the presence and frequently the quantity of the components separated by the column 103. Generally, the detector 105 is a known GC detector such as a flame ionization detector (FID), a mass spectrometer detector (MSD), a thermal conductivity detector (TCD), an electron capture detector (ECD), a nitrogen phosphorus detector (NPD), a sulfur chemiluminescence detector (SCD), a nitrogen chemiluminescence detector (NCD), a pulsed flame photometric detector (PFPD), a helium ionization detector (HID), or a flame photometric detector (FPD).

The GC system 100 also comprises a controller 106 and a power source 107. The controller 106 may be one of a plurality of controllers (not shown) of the GC system 100, or may be the sole controller of the GC system. Presently, the function of the controller 106 with respect to maintaining the heating of the column 103 by the column temperature control apparatus 104 is described. Other functions of the controller 106 or of other controllers are not germane to the present teachings and are not described.

Generally, the controller 106 can be implemented in numerous ways (e.g., such as with dedicated hardware) to perform various functions discussed herein. A "processor" is one example of a controller, which employs one or more microprocessors that may be programmed using software (e.g., microcode) to perform various functions discussed herein. The controller 106 may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, microcontrollers, application specific integrated circuits (ASICs), and field-programmable gate arrays (FPGAs).

In various implementations, the controller 106 may be associated with one or more storage media (generically referred to herein as "memory," e.g., volatile and non-volatile computer memory such as random-access memory (RAM), read-only memory (ROM), programmable read-only memory (PROM), electrically programmable read-only memory (EPROM), electrically erasable and programmable read only memory (EEPROM), universal serial bus (USB) drive, floppy disks, compact disks, optical disks, magnetic tape, etc.). In some implementations, the storage media may be encoded with one or more programs that, when executed on the controller 106, perform at least some of the functions discussed herein. Various storage media may be fixed within the controller 106 or may be transportable, such that the one or more programs stored thereon can be loaded into a processor or controller so as to implement various aspects of the present teachings discussed herein. The terms "program" or "computer program" are used herein in a generic sense to refer to any type of computer code (e.g., software or microcode) that can be employed to program the controller 106.

The controller 106 is configured to receive temperature data from a temperature sensor (not shown in FIG. 1), and based on the temperature data, is configured to provide control signals to the power source 107. The power source 107 is one of a number of known electrical power sources and is configured to adjust the power of the column temperature control apparatus 104 to maintain the temperature of the column 103 at approximately a desired temperature.

Figure 2A:
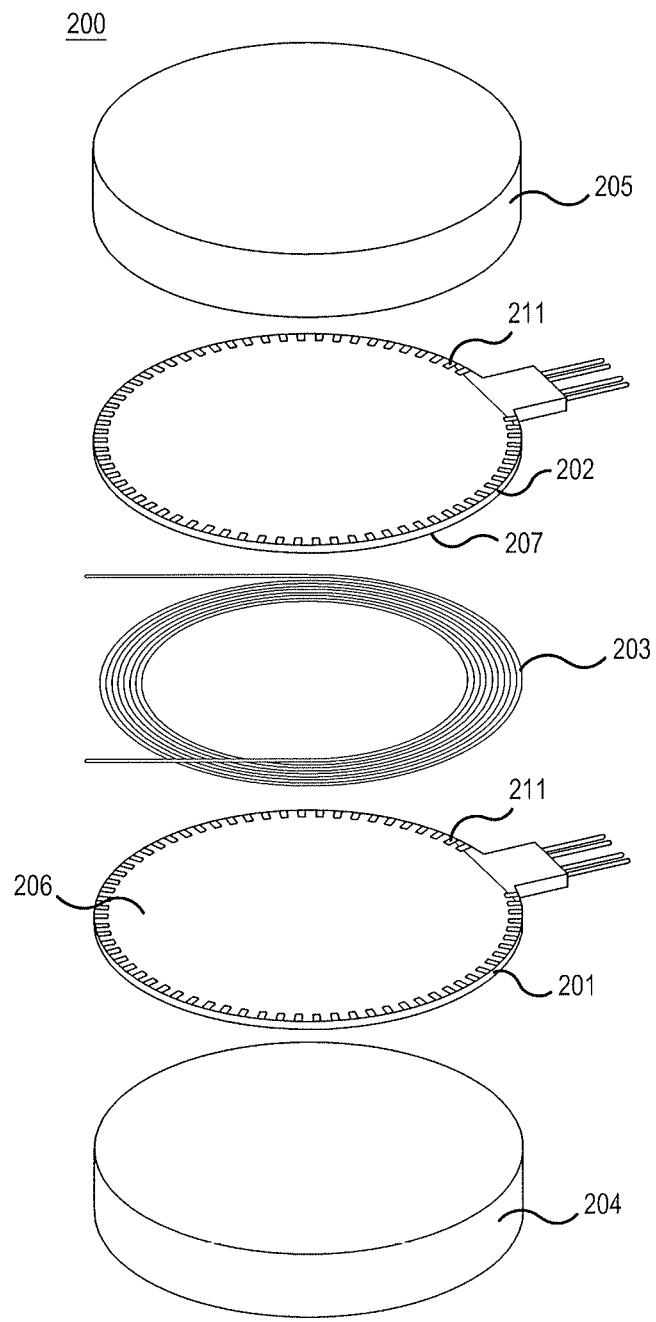
FIG. 2A shows an exploded view of an apparatus for heating a GC column in accordance with a representative embodiment.

FIG. 2A shows an exploded view of a column temperature control apparatus 200 (sometimes referred to as "an apparatus") for heating a GC column 203 in accordance with a representative embodiment. The column temperature control apparatus 200 comprises a first column heating apparatus 201 and a second column heating apparatus 202. Notably, the column temperature control apparatus 200 of the present embodiment is contemplated for use as the column temperature control apparatus 104 in GC system 100 described above.

An optional first insulation layer 204 is disposed below the first column heating apparatus 201 and an optional second insulation layer 205 is disposed above the second column heating apparatus 202. The GC column 203 is disposed above an upper side 206 of the first column heating apparatus 201, and below a lower side 207 of the second column heating apparatus 202 with the lower side 207 of the second column heating apparatus 202 opposing the upper side 206 of the first column heating apparatus 201. As described more fully below, heat flows through the upper side 206 of the first column heating apparatus 201 and the lower side 207 of the second column heating apparatus 202, which is ultimately transferred to the GC column 203.

Each of the first and second column heating apparatuses 201, 202 includes a grommet 211 that is used to secure the various layers of the first column heating apparatus 201 and the second column heating apparatus 202. Illustratively, the grommet 211 comprises stainless steel. Other means of securing the layers are also contemplated, such as brackets, clips etc. The requirements of the grommet or other securing means are that it can tolerate elevated temperatures (e.g.

450° C.) and still maintain sufficient pressure on the first and second column heating apparatuses 201, 202. High temperature metals are the preferred material.

The GC column 203 is wound in a substantially spiral manner, and can have portions of the column "stacked" over other portions of the column. Persons skilled in the art would appreciate how a GC column 203 may be "stacked" or "wound" to achieve the desired objectives described herein. When stacked or wound, the GC column 203 may have a plurality of layers in cross-section. The GC column may also be formed by stacking two or more independent columns on top of each other, each wound in a spiral manner. This, again, would result in the GC column 203 having a plurality of layers in cross-section. If one side of the GC column 203 is actively heated through contact with a heating element, and another side is not, even if the GC column is in the form of a single-layer Archimedean spiral, the heating of the GC column can be uneven. This non-uniformity can cause thermal gradients to form across the GC column. These effects can be exacerbated when the GC column is wound or "stacked" in a plurality of layers in cross-section. By providing heat to both the "top" and the "bottom" of the GC column 203 resting between the substantially flat surfaces of the first and second sides 206, 207 of the first and second column heating apparatuses 201, 202, the GC column 203 can be more uniformly heated during a sample run. Similarly, by providing active heating on both sides, when the GC column 203 is a set of two or more columns on top of each other, each column will be less susceptible to thermal gradients and see a more similar thermal environment.

Additionally, by providing heat to both the "top" and the "bottom" of the GC column 203 resting between the substantially flat surfaces of the first and second sides 206, 207 of the first and second column heating apparatuses 201, 202, thermal ambient rejection is also significantly improved compared to known GC heating arrangements (e.g., single heater arrangements) because both sides of the GC column 203 are temperature controlled surfaces. If GC column 203 were only disposed over first column heating apparatus 201, and not "sandwiched" between first and second column heating apparatuses 201, 202 as depicted in the representative embodiment of FIG. 2A, one side of the GC column 203 contacts the first surface, while the other is either in contact with first layer of insulation 204, or is simply exposed to air. The first layer of insulation 204 is in contact with air so in either case, the ambient temperature of the air impacts the temperature of the portion of the GC column 203 not in direct contact with the first column heating apparatus 201. Influence of changes in ambient temperature on the column temperature during an analysis results in shifts in retention time of an analyte that can make an analyte difficult to identify or make an analysis less repeatable. By providing the GC column 203 between the first and second column heating apparatuses 201, 202, the thermal environment of the GC column 203 can be isolated from the ambient temperature and therefore the retention time of the analytes better controlled.

Figure 2B:
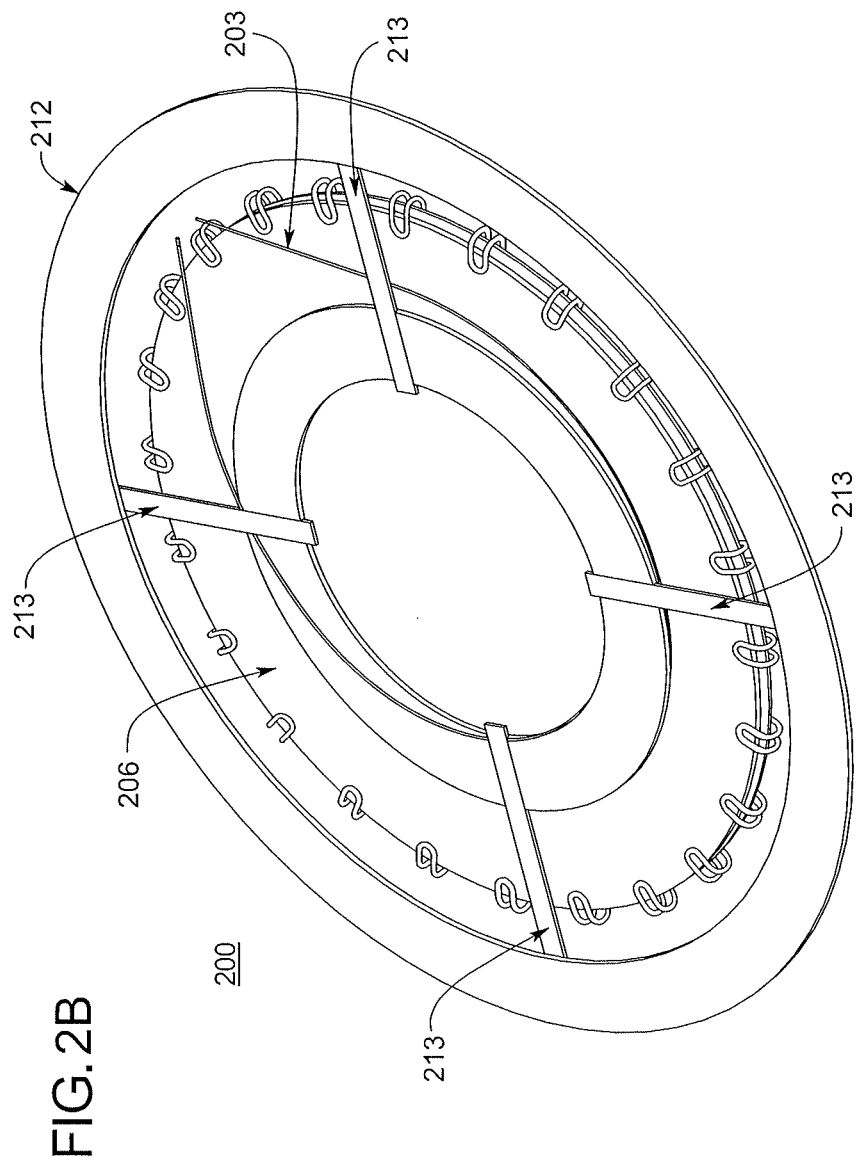
FIG. 2B shows the apparatus for heating a GC column of FIG. 2A after a representative assembly with a representative column mounting scheme.

FIG. 2B shows the temperature control apparatus 200 of FIG. 2A having the GC column 203 disposed thereover (without the second heating apparatus 202 or insulation layers 205, 204 shown), in accordance with another representative embodiment. As can be appreciated, the first column heating apparatus 201 of FIG. 2B shares certain aspects, details and features common to those of the first column heating apparatus 201 described in connection with FIG. 2A above. Often, such common aspects, features and details are not repeated. As noted above, the GC column 203 is oriented in a comparatively flat spiral and is disposed over the upper side 206 of the first column heating apparatus 201, and makes thermal contact with the upper side 206. Again, the coiling of GC column 203 in representative embodiments may be a substantially planar spiral having one or more "stacked" so that the GC column 203 is in thermal contact with the first and second column heating apparatuses 201,202, which are substantially planar, as described above. In accordance with the depicted representative embodiment, the GC column 203 is held in place over the first side 206 by GC column supports 213 mounted to GC column bracket 212. Illustratively, the GC column supports 213 can be constructed of thin strips of metal such as aluminum, nickel, or stainless steel. More generally, the GC column supports 213 may be made of a material that is able to support the GC column 203 on the upper side 206 and tolerate the temperature exposure (up to 450° C.). The GC column bracket 212 serves as a structural element for GC column 203 and ensures repeatable positioning of the GC column 203 on upper side 206 for reproducible chromatographic performance. The GC column bracket 212 can be mounted in the GC system using one or more of a variety of known elements including, but not limited to, screws, clamps, and magnets (not shown). Notably, the GC column bracket 212 and supports 213 are contemplated for use alternatively with the second column heating apparatus 202.

Figure 3A:
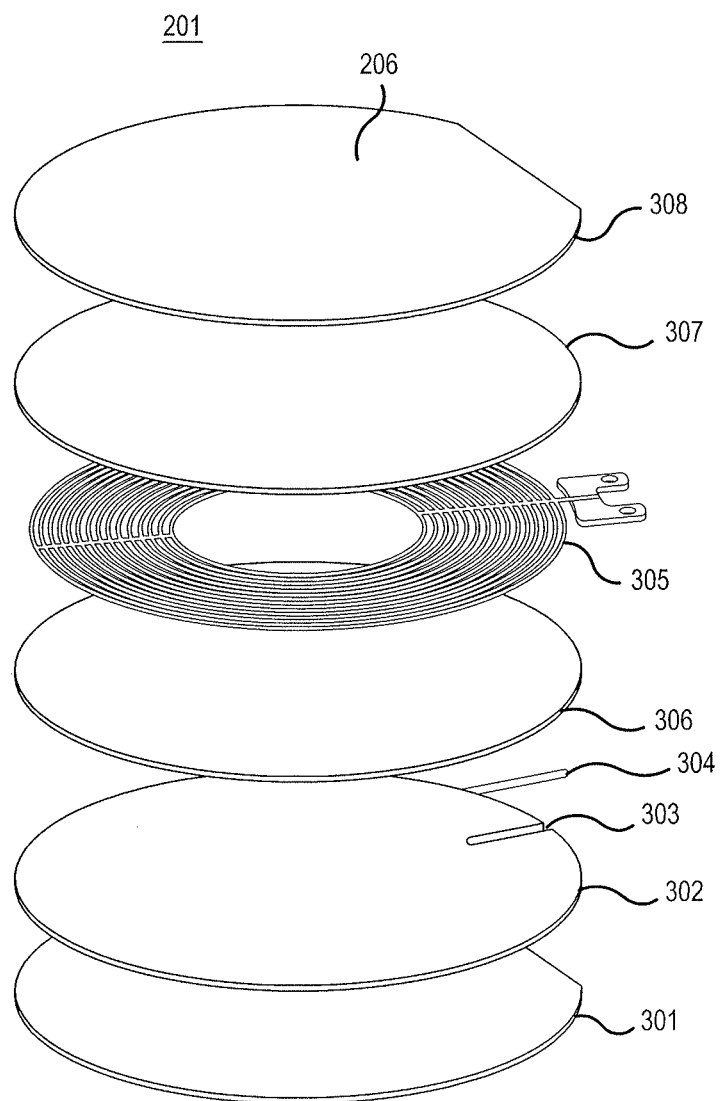
FIG. 3A shows an exploded view of a column heating apparatus in accordance with a representative embodiment.

FIG. 3A shows an exploded view of first column heating apparatus 201 for heating a GC column (not shown) in accordance with a representative embodiment.

The first column heating apparatus 201 comprises a first substrate 301, which is substantially planar. A first spacer layer 302 is optionally disposed above or adjacent to the first substrate 301. A first recess 303 is provided in the first spacer layer 302, and is configured to receive a first temperature sensor 304.

The first column heating apparatus 201 comprises a first heating element 305 disposed between an optional first intervening layer 306 and an optional second intervening layer 307. The first and second intervening layers 306, 307 are generally made from the same material.

While the first heating element 305 is shown as a substantially uniform series of traces, it is also contemplated that that the traces may be substantially non-uniform, non-symmetrical, and/or irregular. By way of example, since the outer edge of the first heating element 305 is more exposed to the external environment, a decrease in temperature may occur at the outer edge compared to the inner portions of the assembly. By increasing density and/or changing the width of the traces of the first heating element 305 at its edge, the power density of the first heating element 305 near the outer edge is increased, and the temperature differential between the inner portion and the outer edge of the heating element, manifest in the noted temperature decrease, may be reduced or eliminated. Further modifications of the thickness of the traces may also have desirable properties as described herein. (Notably, the non-uniform, non-symmetrical, and/or irregular distribution of traces, which is described in connection with first heating element 305, is also contemplated for second heating element 305', as described in FIG. 3B.)

First and second intervening layers 306, 307 may be selected to act as electrical insulators between the first heating element 305 and the first substrate 301 and a second substrate 308. Like the first substrate 301, the second substrate 308 is substantially planar. The second substrate 308 is configured to have the GC column (not shown in FIG. 3A) in thermal contact therewith. The GC column is in thermal contact with the second substrate 308 through either direct contact or within a substantially close proximity to transfer heat. Alternatively, the second substrate 308 may be in thermal contact with the GC column despite the presence of an intervening layer (not shown) between the GC column and the second substrate 308. The intervening layer may be, for example, a layer of thermally conductive material to improve thermal conduction to the GC column. Illustratively, the GC column is adjacent to the first side 206 of the first column heating apparatus 201, and heat from the first column heating apparatus 201 is transferred through the second substrate 308 to the GC column. As can be appreciated from a review of FIG. 3A, the first side 206 is substantially planar.

The first and second substrates 301, 308 may comprise single layer or multiple layers of the same or different materials. As described more fully below, the first column heating apparatus 201 substantially uniformly heats the GC column contacting the second substrate 308 at the first side 206.

In known GC heaters, such as air convection ovens, the oven may require large amounts of power (up to 2000 W) to allow temperature programming rates of 30-60° C./min. By contrast, as described more fully below, the first column heating apparatus 201 beneficially provides similar temperature programming rates at substantially less than 100 W. In addition, the first column heating apparatus 201 allows much faster temperature programming rates (e.g., up to five to ten times faster than a known GC heater with 25% of the power requirement of the known GC heater), resulting in faster chromatographic analyses. Also, where known GC heaters may take six or more minutes to cool from 450° C. to 50° C., the first column heating apparatus 201 may take less than three minutes allowing for faster cycle times between analyses. The first column heating apparatus 201 realizes these improvements in performance by specifying the material properties of the second substrate 308 or the first and second substrates 301, 308 to be low thermal mass while maintaining mechanical stiffness, small thermal gradients, and resistance to thermal deformation.

As should be appreciated by one of ordinary skill in the art, the "thermal mass" of an object is a measure of its capacity to store thermal energy (i.e., heat). As such, a material that has a comparatively low thermal mass will require less heat in order to change temperature than one of comparatively high thermal mass. As described more fully below, in order to enable faster heating and cooling, the materials selected for the first and second substrates 301, 308 and the first column heating apparatus 201 have a low thermal mass.

Thermal mass (with units of J/K) is the product of the specific heat of the material, $c_p$, and the mass of the object, m. For convenience, mass can be further specified as the product of the density, $\rho$, of the material, a surface area, $A_s$, and a thickness, t, normal to the surface area. Combining, thermal mass can be expressed as:

thermal mass=$(\rho c_p t A_s)$

Since the surface area of the first column heating apparatus 201 is fixed based on the size of the column to be heated, the surface area is viewed as a constant for this discussion. The remaining terms are examined further. The term, $\rho c_p$, is also known as the volumetric heat capacity of the material and is an intrinsic property of the material. To minimize thermal mass, this term should be minimized. According to a representative embodiment, materials for the second substrate 308 or the first and second substrates 301, 308 have a volumetric heat capacity less than approximately $$3.0 \times 10^6 \frac{J}{m^3 k} \text{ at } 25° \text{ C.}$$

The selection of material for the second substrate 308 or the first and second substrates 301, 308 is additionally bound by mechanical stiffness, low thermal gradients, and resistance to thermal deformation. These bounds are particularly important in determining the minimum thickness of material required for the second substrate 308 or the first and second substrates 301, 308. Along with thermal mass, these are not independent characteristics, so choice of materials is made considering all of them. The ultimate goal is to achieve low thermal gradients across the first side 206 of second substrate 308 while achieving a relatively low thermal mass for first and second substrates 301 and 308 to enable faster heating and cooling.

Thermal gradients across the second substrate 308 or across the first and second substrates 301, 308 result from different parts of the substrates being in different thermal environments. The first heating element 305, for instance, does not have a completely homogenous thermal profile. In addition, the outer edges of the first and second substrates 301, 308 will typically have more exposure to the ambient temperature environment. As such, thermal gradients can exist across the first and second substrates 301, 308. Gradients are reduced when the material chosen for the first and second substrates has low resistance to heat flow, that is, a high thermal conductivity, k. It is desirable, therefore, to have a material with comparatively high thermal conductivity, particularly for the second substrate 308, so that the first side 206 that touches the GC column is substantially uniform in temperature. According to a representative embodiment, materials for the second substrate 308 or the first and second substrates 301, 308 have a thermal conductivity greater than approximately $$100 \frac{W}{mK} \text{ at } 25° \text{ C.}$$

The first and second substrates, 301 and 308, provide mechanical structure for the first column heating apparatus 201. Notably, the first and second substrates 301, 308 support the relatively non-rigid first column heating element 305, the optional layers 306 and 307, as well as the first spacer layer 302 and the first temperature sensor 304. Beneficially, materials chosen for the first and second substrates 301, 308 are sufficiently stiff to provide adequate support. The stiffness of a material is related to its elastic modulus (or Young's Modulus), E. If a material has a high elastic modulus, then a thinner cross-section is necessary to provide the same stiffness as a material with a lower elastic modulus. It is beneficial, therefore, to have a material with a high elastic modulus so that less (thermal) mass of material is required to achieve adequate stiffness. According to a representative embodiment, materials for the first and second substrates 301, 308 have a Young's Modulus greater than approximately 100 GPa. In addition to stiffness, the first and second substrates, 301 and 308 must maintain surface flatness in order to hold the heater and column in direct contact with the first side 206, or in indirect contact with the first side 206 (i.e., with the above-mentioned intervening layer (not shown) between the GC column 203 and the first side 206). Issues in flatness may occur due to deformation or "buckling" from rapid temperature changes. If large thermal gradients exist in a component such as, for example, when the component is cooled asymmetrically, sections of the component will want to grow due to thermal expansion while other sections will want to remain fixed. In the worst case, this can cause buckling or fracture.

The likelihood of mechanical deformation due to thermal expansion can be minimized by choosing a material with a high thermal conductivity, k, low thermal expansion coefficient, α, or both. A material with high thermal conductivity resists the formation of large thermal gradients within the material. Materials with low thermal expansion do not grow very much even under significant thermal gradients. Choosing materials with a high thermal conductivity, low thermal expansion coefficient, or both, allows for the use of less material (e.g., a thinner piece of it) and therefore less thermal mass while providing adequate resistance to buckling. According to a representative embodiment, materials for the second substrate 308 or the first and second substrates 301, 308 have a ratio of thermal conductivity to coefficient of thermal expansion greater than approximately $$25 \frac{W}{m(ppm)} \text{ at } 25° \text{ C.}$$

Another consideration in the selection of the material for the second substrate 308, or the first and second substrates 301, 308 is the electrical insulating properties of the material. Beneficially, the material is substantially electrically insulating to avoid having to add an additional material in the stack of the first and second column heating apparatuses 201, 202 to perform this function.

Finally, it is important to select a material for the second substrate 308, or the first and second substrates 301, 308 that is operative in the first and second column heating apparatuses 201, 202 at temperatures greater than approximately 450° C.

Table 1 presents a summary of some of the factors to be considered in selection of the material for the second substrate 308, or the first and second substrates 301, 308.

TABLE 1

| Issue Addressed | Parameter | Maximize or Minimize Parameter |
|---|---|---|
| Thermal Mass | ρc_p (Volumetric Heat Capacity) | Minimize |
| Thermal Gradients | k (Thermal Conductivity) | Maximize |
| Buckling/CTE | k/α (Thermal Conductivity/Coefficient of Thermal Expansion) | Maximize |
| Mechanical Stiffness | E (Young's Modulus) | Maximize |

In a representative embodiment, the second substrate 308 comprises silicon. The silicon may be monocrystalline silicon or polycrystalline silicon. Generally, the silicon layer that forms the second substrate 308 has a thickness of approximately 0.3 to 1.5 mm. Illustratively, the second substrate 308 comprises <1,0,0>Si having a thickness of approximately 0.675 mm. In a representative embodiment, first substrate 301 comprises <1,0,0>Si wafer having a thickness of approximately 0.675 mm, and the second substrate 308 comprises two <1,0,0>Si wafers each having a thickness of approximately 0.675 mm each. It was discovered that the use of two wafers for second substrate 308 provides somewhat improved retention time repeatability. Notably, the second substrate 308 does not require special polishing or doping. Moreover, and although not essential, the first substrate 301 may be made of the same material and to the same specifications as the second substrate 308.

It is noted that the use of silicon for the second substrate 308, or the first and second substrates 301, 308 is merely illustrative. More generally, the materials selected for the second substrate 308, or the first and second substrates 301, 308 are selected to have a volumetric heat capacity (ρc_p) less than approximately $$3.0 \times 10^6 \frac{J}{m^3 k} \text{ at } 25° \text{ C.};$$

a thermal conductivity (k) greater than approximately $$100 \frac{W}{mK} \text{ at } 25° \text{ C.};$$

a ratio of thermal conductivity to coefficient of thermal expansion $$\left(\frac{k}{\alpha}\right)$$

greater than approximately $$25 \frac{W}{m(ppm)} \text{ at } 25° \text{ C.};$$

and a Young's Modulus (E) greater than approximately 100 GPa.

These physical characteristic are desired in order to achieve faster heating and cooling of the first column heating apparatus 201 within several bounds including low thermal mass, mechanical stiffness, low thermal gradients and resistance to deformation. Table 2 compares these four characteristics across a range of materials.

TABLE 2

| Parameter | Silicon | Aluminum | Aluminum Nitride | Pyrex | Diamond | Silicon Carbide | Copper | Tungsten | 85% Tungsten 15% Copper | Molybdenum |
|---|---|---|---|---|---|---|---|---|---|---|
| ρc_p(10^6 J/cm^3K) | 1.64 | 2.43 | 2.44 | 1.67 | 1.80 | 2.05 | 3.42 | 2.58 | 2.85 | 2.55 |
| k(W/mK) | 130 | 205 | 140 | 1 | 1000 | 300 | 401 | 174 | 215 | 138 |
| k/α(W/m-ppm) | 50 | 8.91 | 31.1 | 0.25 | 847 | 108 | 23.6 | 40.5 | 28.9 | 27.6 |
| E(GPa) | 130 | 69 | 308 | 64 | 1220 | 450 | 117 | 400 | 310 | 329 |

Based on the foregoing, the material selected for the second substrate 308, or the first and second substrates 301, 308 preferentially has a volumetric heat capacity less than approximately $$3.0 \times 10^6 \frac{J}{cm^3 K} \text{ at } 25^\circ \text{ C.}$$

Therefore, copper, alumina, nichrome, stainless steel, nickel, sapphire, silicon nitride, tungsten carbide, beryllium oxide, brass, bronze, aluminum brass, iron, and beryllium are not preferred materials for the second substrate 308, or the first and second substrates 301, 308.

The material selected for the second substrate 308, or the first and second substrates 301, 308 should have a thermal conductivity greater than approximately $$100 \frac{W}{mK} \text{ at } 25^\circ \text{ C.}$$

Therefore, Pyrex glass, mica, titanium, quartz glass, gallium arsenide, germanium, boron nitride, zirconium oxide, boron carbide, indium phosphide, niobium, rhenium, and tantalum are generally not preferred materials for the second substrate 308, or the first and second substrates 301, 308.

The material selected for the second substrate 308, or the first and second substrates 301, 308 additionally should have the ratio of thermal conductivity, k, to the coefficient of thermal expansion, α, that is greater than approximately $$25 \frac{W}{m\{ppm\}} \text{ at } 25^\circ \text{ C. (at } 25^\circ \text{ C.)}.$$

Therefore, aluminum, as shown in the table, as well as magnesium, silver, zinc, and gold are not preferred materials for the second substrate 308, or the first and second substrates 301, 308.

The material selected for the second substrate 308, or the first and second substrates 301, 308 additionally should have a Young's Modulus greater than approximately 100 GPa. Therefore, graphite is not a preferred material for the second substrate 308, or the first and second substrates 301, 308.

Based on the analysis above, illustrative materials that can be used for the second substrate 308, or the first and second substrates 301, 308 and meet all of the preferred material characteristics comprise silicon, aluminum nitride, diamond, silicon carbide, tungsten, molybdenum, alloys of tungsten (particularly with copper), alloys of molybdenum (particularly with copper), and combinations thereof.

The first heating element 305 can be disposed between the optional first intervening layer 306 and the optional second intervening layer 307. The first and second intervening layers 306, 307 are generally made from the same material, and each have a second comparatively low thermal mass. Moreover, the first and second intervening layers 306, 307 are each made from a material that is electrically insulating. Notably, if the first and second substrates 301, 308 are electrically insulating, the first and second intervening layers 306, 307 can be foregone. However, if the material can become more electrically conducting at comparatively high temperatures (e.g., silicon), then electrical insulation is needed between the heating element and first and second substrates 301, 308 when they are silicon. As such, in a representative embodiment in which first and second substrates 301, 308 are silicon, first and second intervening layers 306, 307 are needed. Notably, however, in another representative embodiment, rather than including first and second intervening layers 306, 307, the sides of the first and second substrates 301, 308 facing the heating element may be coated with a layer of glass or other dielectric to perform this insulating function.

The first heating element 305 is illustratively a resistive heating element, such as wire heater or a foil heater. Other types of heating elements are contemplated. As should be appreciated, the heating element is beneficially quite thin, and thereby does not substantially interfere with the desirably flat nature of each of the layers of the first and second column heating apparatuses 201, 202. With known thin film fabrication methods, such comparatively thin heating elements that are within the purview of one of ordinary skill in the art are contemplated.

Like the comparatively low thermal masses of the first and second substrates 301, 308, the comparatively low thermal mass of the optional first and second intervening layers 306, 307 ensures they heat comparatively quickly and will not retain heat very well. As such, the column heating apparatus 201 can be heated quickly across its surface, and will not retain heat to the extent as other materials often used in heaters. Again, the former attribute ensures ultimately that the GC column disposed over first side 206 of the second substrate 308 is heated comparatively very quickly, which improves analysis time. The latter attribute enables the thorough dissipation of heat from the first column heating apparatus 201 in a relatively quick and efficient manner enabling faster cycle times and improved retention time repeatability.

In a representative embodiment, the first and second intervening layers 306, 307 each comprise mica, which are of sheet silicate (phyllosilicate) minerals. Generally, mica materials are $X_2Y_{4-6}Z_8O_{20}(OH,F)_4$ in which X is K, Na, or Ca or less commonly Ba, Rb, or Cs; Y is Al, Mg, or Fe or less commonly Mn, Cr, Ti, Li, etc.; Z is chiefly Si or Al, but also may include $Fe^{3+}$ or Ti. The use of mica for first and second intervening layers 306, 307 is merely illustrative, and other materials having similar thermal mass, electrical conductivity, and resistance to mechanical distortion due to rapid temperature change as mica are contemplated. For example, fabrics such as fiberglass, and basalt provide the desired properties.

Generally, the mica layers that form the optional first and second intervening layers 306, 307 of the first column heating apparatus 201 each have a thickness of approximately 0.3 mm. More generally, the material selected for the first and second intervening layers 306, 307 of the first column heating apparatus 201 has an electrical resistivity of approximately $1 \times 10^{12}$ Ω·m to approximately $1 \times 10^{14}$ Ω·m, or greater. Since mica has a comparatively low coefficient of thermal expansion (CTE), similar to silicon, it will not expand when heated or cooled and will not suffer from mechanical distortion. Furthermore, the mica is inherently flat and affords intimate contact between the substrate and the heating element. Other materials that could serve as an electrical insulator in place of mica are, for example, aluminum nitride, quartz, glass, silicon carbide, and the fabrics cited above. Compliant materials like the fabrics cited previously need not be as flat as they can be compressed to achieve intimate contact.

First spacer layer 302 is optionally disposed over the first substrate 301 and beneath the first intervening layer 306 of the column heating apparatus 201. The first spacer layer 302 is a spacer that accommodates first temperature sensor 304. Illustratively, first spacer layer 302 is a compliant material, such as a glass fiber material. The first spacer layer 302 beneficially maintains substantially uniform pressure between the optional first intervening layer 306 of the first heating element 305 and the first substrate 301. Notably, the inclusion of the first temperature sensor 304 can compromise the substantially uniform pressure in the absence of the first spacer layer 302. Non-uniform pressure between the first intervening layer 306 of the column heating apparatus 201 and the first substrate 301 can result in a reduction in the overall "flatness" of the first column heating apparatus 201, leading to thermal gradients and "hot spots," and can thus compromise performance of the GC column.

Figure 3B:
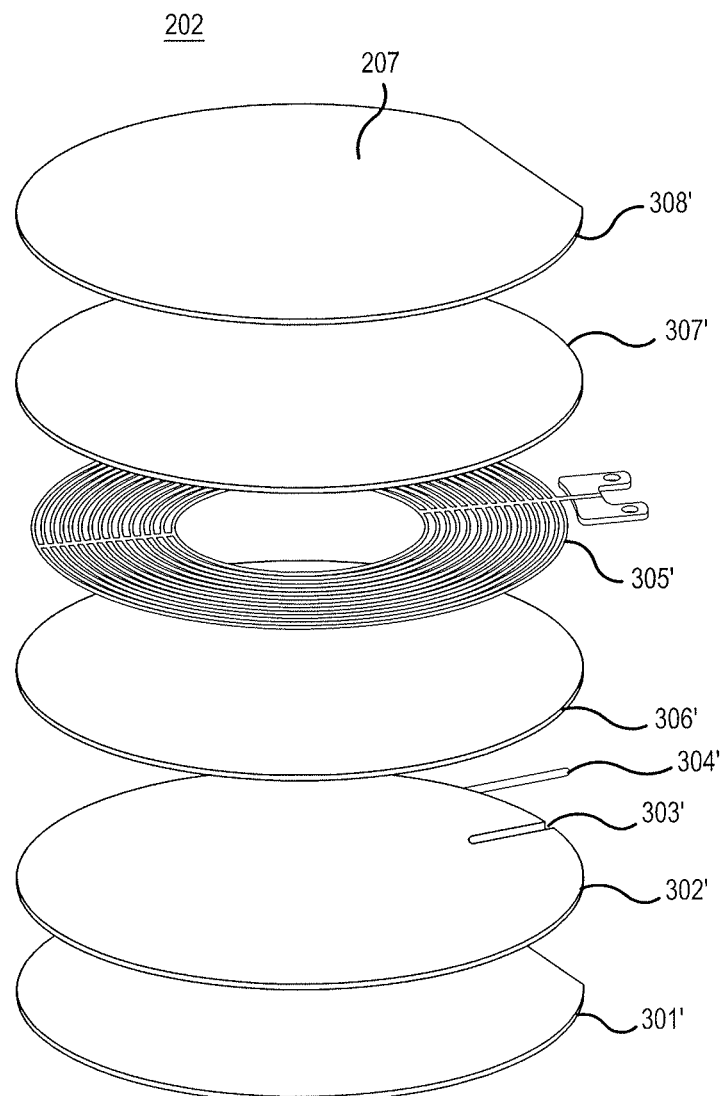
FIG. 3B shows an exploded view of a column heating apparatus in accordance with a representative embodiment.

FIG. 3B shows an exploded view of second column heating apparatus 202 for heating a GC column (not shown in FIG. 3B) in accordance with a representative embodiment. Notably, second column heating apparatus 202 is substantially identical to the first column heating apparatus 201 described herein, and comprises the same components of the first column heating apparatus 201. As such, common details of the various components of the second column heating apparatus are often not repeated.

The second column heating apparatus 202 comprises a third substrate 301', which is substantially planar. A second spacer layer 302' is optionally adjacent to the third substrate 301'. A second recess 303' is provided in the second spacer layer 302', and configured to receive a second temperature sensor 304'.

The second column heating apparatus 202 comprises a second heating element 305' disposed between an optional third layer 306' and an optional fourth layer 307'. Third and fourth layers 306', 307' may be selected to act as electrical insulators between the second heating element 305' and the third substrate 301' and a fourth substrate 308'. Like the third substrate 301', the fourth substrate 308' is substantially planar. The fourth substrate 308' is configured to have the GC column (not shown in FIG. 3B) in direct contact therewith. Alternatively, the fourth substrate 308' may be configured to have the GC column in indirect contact therewith, by having an intervening layer (not shown) between the GC column and the fourth substrate 308'. The intervening layer may be, for example, a layer of thermally conductive material to improve thermal conduction to the GC column.

Notably, in operation the second column heating apparatus 202 depicted in FIG. 3B is rotated 180° (i.e., as depicted in FIG. 2A) so that the GC column 203 is disposed below the lower side 207 of the second column heating apparatus 202, and heat from the second column heating apparatus 202 is transferred through the fourth substrate 308' to the GC column. As can be appreciated from a review of FIG. 3B, the second side 207 is substantially planar.

The third and fourth substrates 301', 308' may comprise single layer or multiple layers of the same or different materials. As described more fully below, the second column heating apparatus 202 substantially uniformly heats the GC column contacting the fourth substrate 308' at the lower side 207 of the second column heating apparatus 202.

As alluded to above, the controller 106 receives temperature data from the first temperature sensor 304, and based on these data provides control signals to the power source 107. Similarly, the controller 106 receives temperature data from the second temperature sensor 304' provided in second column heating apparatus 202, and based on these data provides control signals to the power source 107. Based on the control signals from the controller 106, the power source 107 adjusts electrical power to the first and second column heating apparatuses 201, 202 to maintain the temperature of the GC column at a substantially constant value or to cause it to change according to some desired and repeatable program.

Figure 3C:
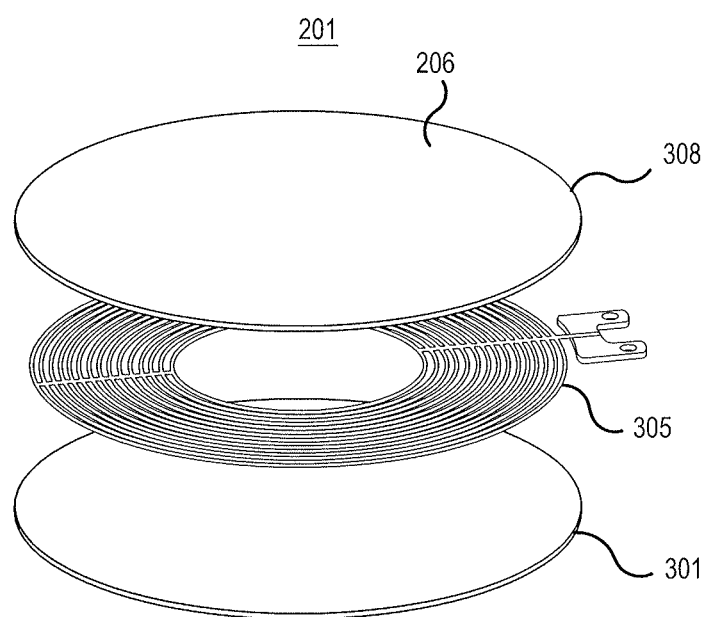
FIG. 3C shows an exploded view of a column heating apparatus in accordance with a representative embodiment.

FIG. 3C shows an exploded view of first column heating apparatus 201 in accordance with another representative embodiment. Many aspects of the first column heating apparatus 201 of this embodiment are similar to those described above. As such, many details of various features that are common to those of first column heating apparatus 201 of the representative embodiment of FIG. 3A are not repeated. Notably, the various characteristics of the common elements of the first and second column heating apparatuses 201, 202 are the same. FIG. 3C depicts a representative embodiment of a first column heating apparatus 201 comprising a first substrate 301 adjacent to a first heating element 305, wherein the optional spacer and first and second intervening layers are omitted.

The first heating element 305 is illustratively a resistive heating element, such as a wire heater or a foil heater. Other types of heating elements are contemplated. As should be appreciated, the first heating element 305 is beneficially quite thin, and thereby does not substantially interfere with the desirably flat nature of each of the layers of the first column heating apparatus 201. With known thin film fabrication methods, such comparatively thin heating elements that are within the purview of one of ordinary skill in the art are contemplated.

The first column heating apparatus 201 also comprises second substrate 308 adjacent to the first heating element 305. The second substrate 308 is configured to have the GC column 203 (not shown in FIG. 3C) in thermal contact therewith. Illustratively, the GC column is disposed over upper side 206 of the second substrate 308, and heat from first heating element 305 is transferred through the second substrate 308 as described above in connection with the representative embodiments of FIGS. 2 and 3A. The first and second substrates 301, 308 may comprise single layer or multiple layers of the same or different materials. Through the heat distribution of the second substrate 308 described above, the first column heating apparatus 201 substantially uniformly heats the GC column contacting the second substrate 308.

In view of this disclosure it is noted that the methods and devices can be implemented in keeping with the present teachings. Further, the various components, materials, structures and parameters are included by way of illustration and example only and not in any limiting sense. In view of this disclosure, the present teachings can be implemented in other applications and components, materials, structures and equipment needed to implement these applications can be determined, while remaining within the scope of the appended claims.

The invention claimed is:

1. An apparatus, comprising:
   a first column heating apparatus, comprising: a first substrate; a second substrate comprising silicon; and a first heating element disposed between the first substrate and the second substrate; and
   a second column heating apparatus, comprising: a third substrate; a fourth substrate comprising silicon; and a second heating element disposed between the third substrate and the fourth substrate.

2. An apparatus as claimed in claim 1, wherein the first and second heating elements are each electrically insulated from their respective substrates.

3. An apparatus as claimed in claim 1, wherein the first and second heating elements each comprise a foil heater or a wire heater.

4. An apparatus as claimed in claim 1, wherein first and third substrates each comprise monocrystalline silicon or polycrystalline silicon.

5. An apparatus as claimed in claim 1, wherein the silicon is monocrystalline silicon or polycrystalline silicon.

6. An apparatus as claimed in claim 1, wherein the silicon is doped with p-type dopants.

7. An apparatus as claimed in claim 1, further comprising a spacer layer disposed between the first heating element and the first substrate, the layer adapted to provide substantially uniform pressure between the heating element and the first substrate.

8. An apparatus as claimed in claim 1, further comprising a spacer layer disposed between the second heating element and the third substrate, the layer adapted to provide substantially uniform pressure between the heating element and the third substrate.

9. An apparatus, comprising:
a first column heating apparatus, comprising: a first substrate; a second substrate having: a volumetric heat capacity less than $3.0 \times [(10)]^6$ J/(m$^3$ K) at 25° C.; a thermal conductivity greater than 100 W/mK at 25° C.; a ratio of thermal conductivity to coefficient of thermal expansion greater than approximately $25 \times [(10)]^6$ W/m at 25° C.; and a mechanical stiffness greater than 100 GPa; and a first heating element disposed between the first substrate and the second substrate; and
a second column heating apparatus, comprising: a third substrate; a fourth substrate having: a volumetric heat capacity less than $3.0 \times [(10)]^6$ J/(m$^3$ K) at 25° C.; a thermal conductivity greater than 100 W/mK at 25° C.; a ratio of thermal conductivity to coefficient of thermal expansion greater than approximately $25 \times [(10)]^6$ W/m at 25° C; and a mechanical stiffness areater than 100 GPa,; and a second heating element disposed between the third substrate and the fourth substrate.

10. An apparatus as claimed in, claim 9, wherein the first and second heating elements are each electrically insulated from their respective substrates.

11. An apparatus as claimed in claim 9, wherein the first and second heating elements each comprise a foil heater or a wire heater.

12. An apparatus as claimed in claim 9, wherein first and third substrates each have: a volumetric heat capacity less than $3.0 \times [(10)]^6$ J/(m$^3$ K) at 25° C.; a thermal conductivity greater than 100 W/mK at 25° C.; a ratio of thermal conductivity to coefficient of thermal expansion greater than approximately $25 \times [(10)]^{\neq}$ W/m at 25° C.; and a mechanical stiffness greater than 100 GPa.

13. An apparatus as claimed in claim 9, further comprising a layer disposed between the first heating element and the first substrate, the layer adapted to provide substantially uniform pressure between the heating element and the first substrate.

14. An apparatus as claimed in claim 9, further comprising a layer disposed between the second heating element and the third substrate, the layer adapted to provide substantially uniform pressure between the heating element and the third substrate.

15. An apparatus, comprising:
a first column heating apparatus, comprising: a first substrate; a second substrate comprising one of: aluminum nitride, diamond, silicon carbide, tungsten, molybdenum or an alloy of tungsten or an alloy of molybdenum; and a first heating element disposed between the first substrate and the second substrate; and
a second column heating apparatus, comprising: a third substrate; a fourth substrate comprising one of: aluminum nitride, diamond, silicon carbide, tungsten, molybdenum or an alloy of tungsten or an alloy of molybdenum; and a second heating element disposed between the third substrate and the fourth substrate.

16. An apparatus as claimed in claim 15, wherein the alloy of tungsten or the alloy of molybdenum comprises copper.

17. An apparatus as claimed in claim 15, wherein the first and second heating elements are each electrically insulated from their respective substrates.

18. An apparatus as claimed in claim 15, wherein each of the first and second heating elements comprises a foil heater or a wire heater.

19. An apparatus as claimed in claim 15, wherein the first and third substrates each comprise one of: aluminum nitride, diamond, silicon carbide, tungsten, molybdenum or an alloy of tungsten or an alloy of molybdenum.

20. An apparatus as claimed in claim 19, wherein the alloy of tungsten or the alloy molybdenum comprises copper.

* * * * *

UNITED STATES PATENT AND TRADEMARK OFFICE
CERTIFICATE OF CORRECTION

PATENT NO. : 10,401,331 B2
APPLICATION NO. : 14/802874
DATED : September 3, 2019
INVENTOR(S) : Paul C Dryden et al.

Page 1 of 2

It is certified that error appears in the above-identified patent and that said Letters Patent is hereby corrected as shown below:

In the Specification

In Column 1, Lines 7-15, delete "The present application claims priority under 35 U.S.C. § 119(e) from: U.S. Provisional Application No. 62/067,924 filed on Oct. 23, 2014, naming Paul Dryden, et al. as inventors; and U.S. Provisional Patent Application No. 62/050,125 filed on Sep. 13, 2014, naming Sammye Traudt, et al. as inventors. The entire disclosures of U.S. Provisional Patent Application Nos. 62/050,125 and 62/067,924 are specifically incorporated herein by reference" and insert -- The present application claims priority under 35 U.S.C. § 119(e) from: U.S. Provisional Application No. 62/067,924 filed on Oct. 23, 2014, naming Paul Dryden, et al. as inventors; and U.S. Provisional Patent Application No. 62/067,407 filed on Oct. 22, 2014, naming Paul Dryden, et al. as inventors. The entire disclosures of U.S. Provisional Patent Application Nos. 62/067,407 and 62/067,924 are specifically incorporated herein by reference. --, therefor.

In Column 6, Line 43, delete "that that" and insert -- that --, therefor.

In Column 10, Lines 45-49, delete "$25 \frac{w}{m\{ppm\}}$" and insert -- $25 \frac{W}{m(ppm)}$ --, therefor.

In Column 11, Lines 35-38, delete "$25 \frac{w}{m\{ppm\}}$" and insert -- $25 \frac{W}{m(ppm)}$ --, therefor.

In the Claims

In Column 15, Line 30, in Claim 9, delete "25×[( 10)]^6" and insert -- 25×[(10)]^6 --, therefor.

In Column 15, Line 39, in Claim 9, delete "25×[( 10)]^6" and insert -- 25×[(10)]^6 --, therefor.

Signed and Sealed this
Twenty-fifth Day of August, 2020

Andrei Iancu
*Director of the United States Patent and Trademark Office*

CERTIFICATE OF CORRECTION (continued)
U.S. Pat. No. 10,401,331 B2

In Column 15, Line 40, in Claim 9, delete "areater" and insert -- greater --, therefor.

In Column 15, Line 41, in Claim 9, delete "GPa,;" and insert -- GPa; --, therefor.

In Column 15, Line 43, in Claim 10, delete "in," and insert -- in --, therefor.

In Column 16, Line 6, in Claim 12, delete "25×[(10)]^≢W/m" and insert -- 25×[(10)]^6 W/m --, therefor.

In Column 16, Line 47, in Claim 20, after "alloy" insert -- of --.